United States Patent
Adolf et al.

(10) Patent No.: US 12,186,546 B2
(45) Date of Patent: Jan. 7, 2025

(54) MEDICAL DEVICE LOADING SYSTEMS, DEVICES, AND METHODS

(71) Applicant: NxStage Medical, Inc., Lawrence, MA (US)

(72) Inventors: Garrick C. Adolf, Burlington, MA (US); Joseph A. Hoell, Jr., Dunbarton, NH (US); Jacob A. Clark, Stoneham, MA (US); Derek Bruce Eldridge, Tyngsborough, MA (US)

(73) Assignee: NxStage Medical, Inc., Lawrence, MA (US)

( * ) Notice: Subject to any disclaimer, the term of this patent is extended or adjusted under 35 U.S.C. 154(b) by 525 days.

(21) Appl. No.: 17/602,614

(22) PCT Filed: Apr. 9, 2020

(86) PCT No.: PCT/US2020/027431
§ 371 (c)(1),
(2) Date: Oct. 8, 2021

(87) PCT Pub. No.: WO2020/210465
PCT Pub. Date: Oct. 15, 2020

(65) Prior Publication Data
US 2022/0193391 A1     Jun. 23, 2022

Related U.S. Application Data

(60) Provisional application No. 62/940,358, filed on Nov. 26, 2019, provisional application No. 62/831,352, filed on Apr. 9, 2019.

(51) Int. Cl.
*A61M 60/847*     (2021.01)
*A61M 1/36*       (2006.01)
(Continued)

(52) U.S. Cl.
CPC ........ *A61M 60/847* (2021.01); *A61M 1/3622* (2022.05); *A61M 1/367* (2013.01);
(Continued)

(58) Field of Classification Search
CPC ...... A61M 1/14; A61M 1/152; A61M 1/3401; A61M 1/3622; A61M 1/362223;
(Continued)

(56) References Cited

U.S. PATENT DOCUMENTS 5,141,492 A    8/1992   Dadson et al.
5,364,592 A    11/1994  Lewis et al.
(Continued)

OTHER PUBLICATIONS

International Search Report and Written Opinion dated Aug. 11, 2020 for International Patent Application No. PCT/US2020/027431.
(Continued)

*Primary Examiner* — Dirk R Bass
(74) *Attorney, Agent, or Firm* — Potomac Law Group, PLLC

(57) ABSTRACT

A cartridge insertion system includes a chassis supporting a fluid circuit, the chassis having a forward end with key pins projecting from the forward end and a rear end. The system also includes a medical treatment device with a slot opening closed by doors having a major dimension and having key openings spaced apart a same distance as the key pins on the chassis, such that when the chassis is pushed toward the slot opening, the key pins enter the key openings before the forward end meets the doors. The key pins push against latches that hold the door locked shut, so that the doors will not open if a cartridge without key pins is pressed against the door. When a cartridge with key pins is used, the doors unlock and allow the cartridge to be inserted.

16 Claims, 7 Drawing Sheets

(51) Int. Cl.
    *A61M 60/113*     (2021.01)
    *B01L 9/00*     (2006.01)

(52) U.S. Cl.
    CPC ............ *A61M 60/113* (2021.01); *B01L 9/527* (2013.01); *A61M 1/362223* (2022.05); *A61M 1/36225* (2022.05); *A61M 1/36226* (2022.05); *A61M 2205/121* (2013.01)

(58) Field of Classification Search
    CPC .......... A61M 1/36225; A61M 1/36226; A61M 1/367; A61M 2205/121; A61M 60/113; A61M 60/847; B01L 9/527
    See application file for complete search history.

(56) References Cited

U.S. PATENT DOCUMENTS

| | | |
|---|---|---|
| 6,852,090 B2 | 2/2005 | Burbank et al. |
| 8,485,800 B2 | 7/2013 | Lanigan et al. |
| 2004/0086423 A1 | 5/2004 | Wohlstadter et al. |
| 2005/0209563 A1 | 9/2005 | Hopping et al. |
| 2008/0217246 A1 | 9/2008 | Benn et al. |
| 2016/0101278 A1 | 4/2016 | Norris et al. |

OTHER PUBLICATIONS

Invitation to Pay Additional Fees dated Jun. 9, 2020 for International Patent Application No. PCT/US2020/027431.
Extended European Search Report dated Nov. 2, 2022 for European Patent Application No. 20786792.0.

MEDICAL DEVICE LOADING SYSTEMS, DEVICES, AND METHODS

CROSS-REFERENCE TO RELATED APPLICATIONS

This Application is a U.S. national stage filing under 35 U.S.C. § 371 of International Application No. PCT/US2020/027431, filed Apr. 9, 2020, which claims priority to and the benefit of U.S. Provisional Patent Application No. 62/831,352 filed Apr. 9, 2019 and U.S. Provisional Patent Application No. 62/940,358 filed Nov. 26, 2019, all of which are hereby incorporated by reference in their entireties.

BACKGROUND

Fluid circuits adapted to cartridge-borne fluid circuits for loading into medical devices are known. See for example, U.S. Pat. No. 6,852,090. There is an on-going need for improvements in the convenience and simplicity of devices for connecting cartridge-borne fluid circuits in medical devices.

SUMMARY

A cartridge loading mechanism unlocks doors of a slot opening of a medical treatment device. Key pins on a cartridge chassis push on latches to force them out of engagement with ridges on the doors which protect the slot opening.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
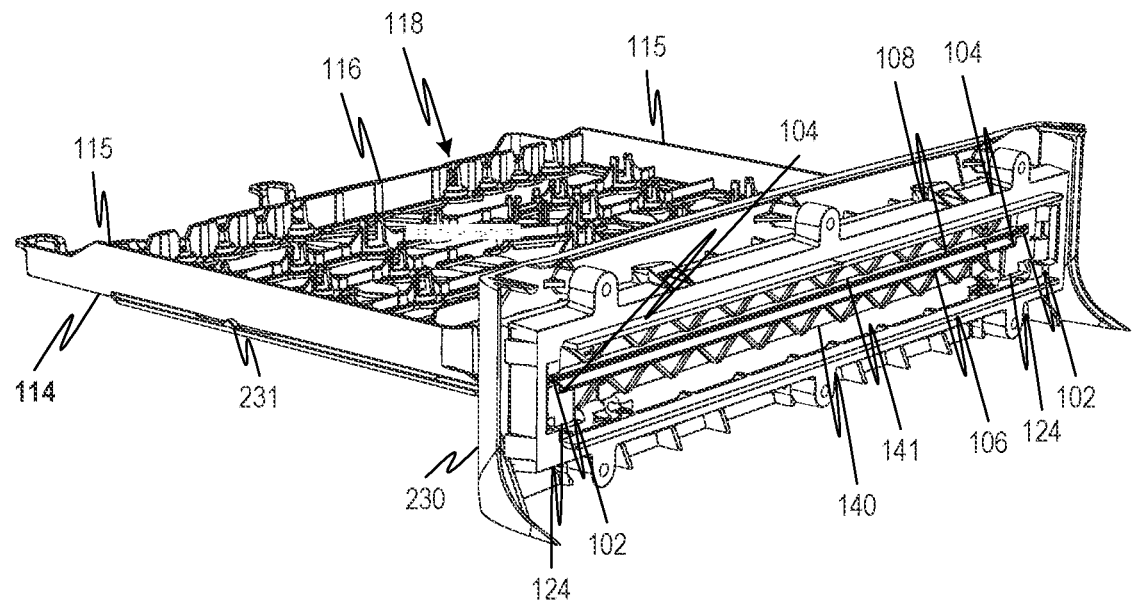
FIGS. 1A, 1B, and 1C show a cartridge chassis configured to support a fluid circuit in position to be loaded into a slot opening of a medical treatment device with only a portion of the housing of the medical treatment device being visible in the drawing according to embodiments of the disclosed subject matter.
Figure 1B:
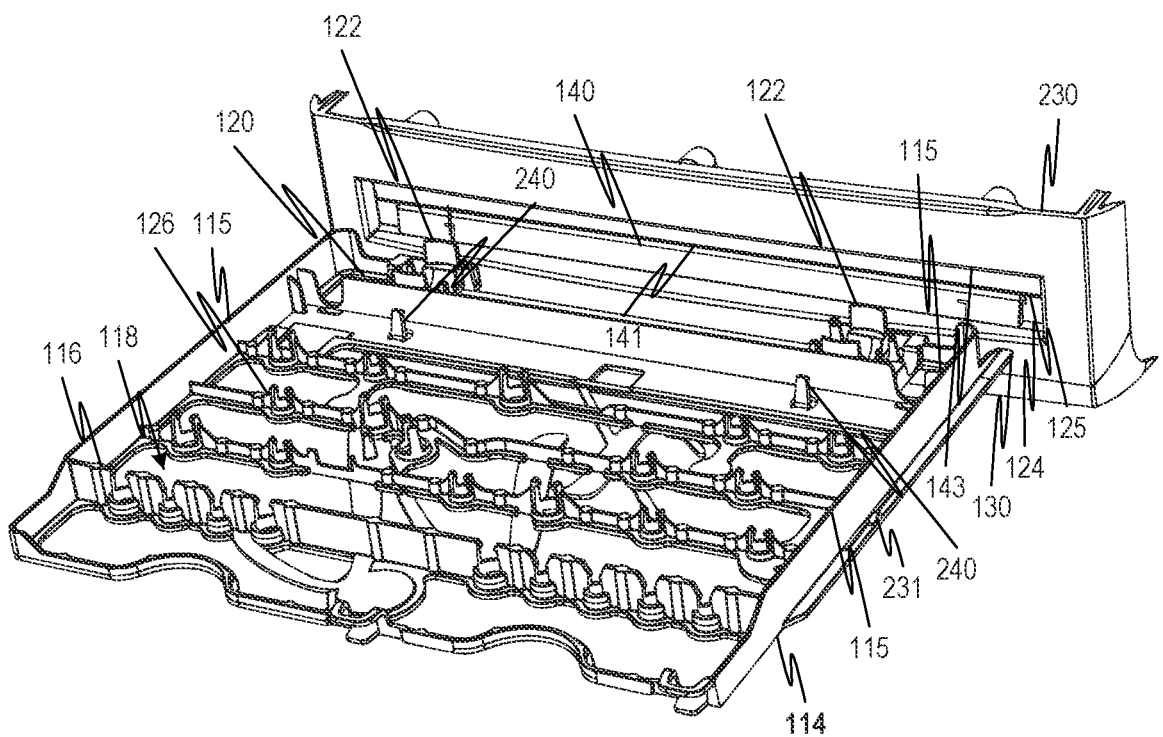
Figure 1C:
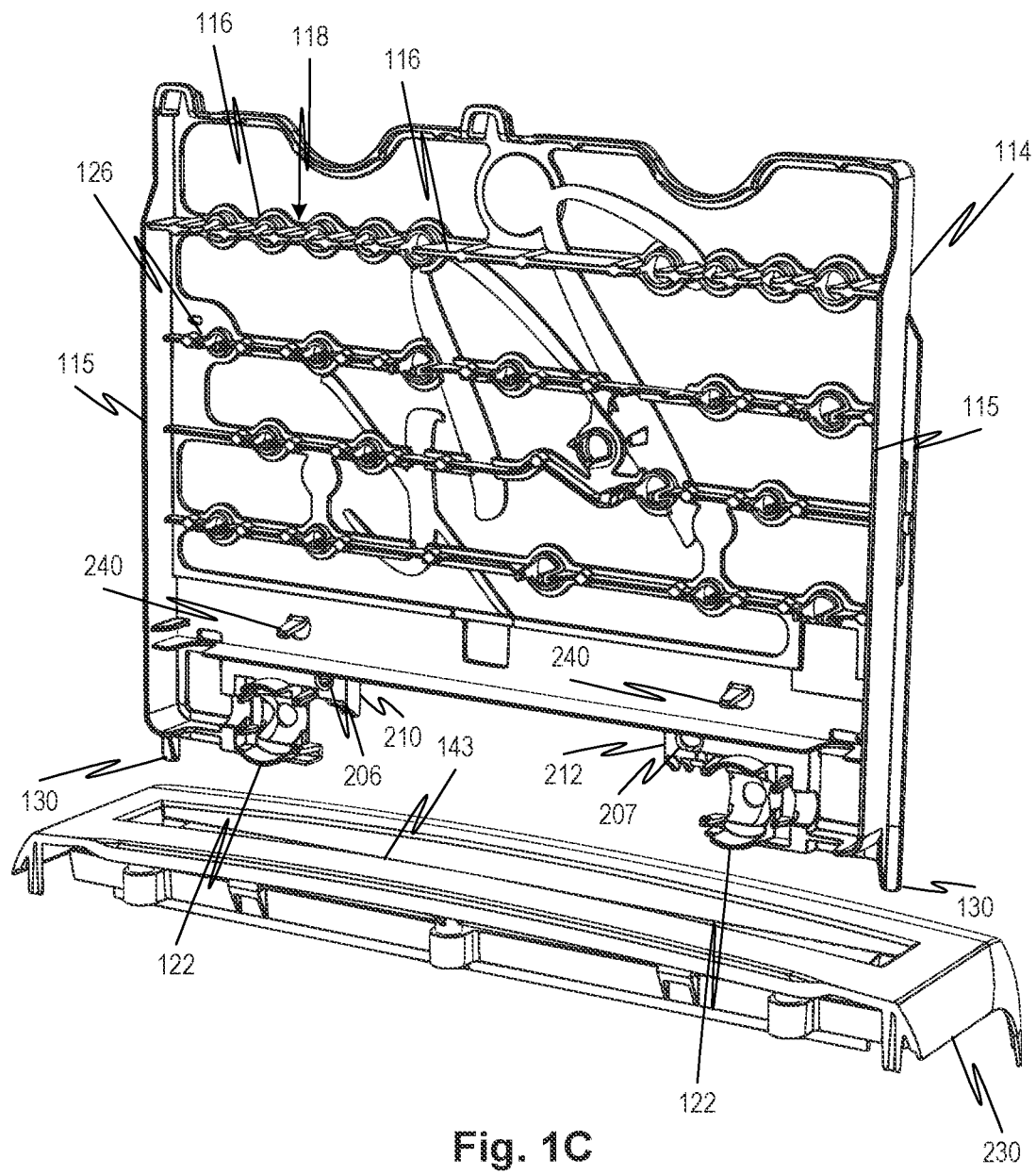
Figure 2A:
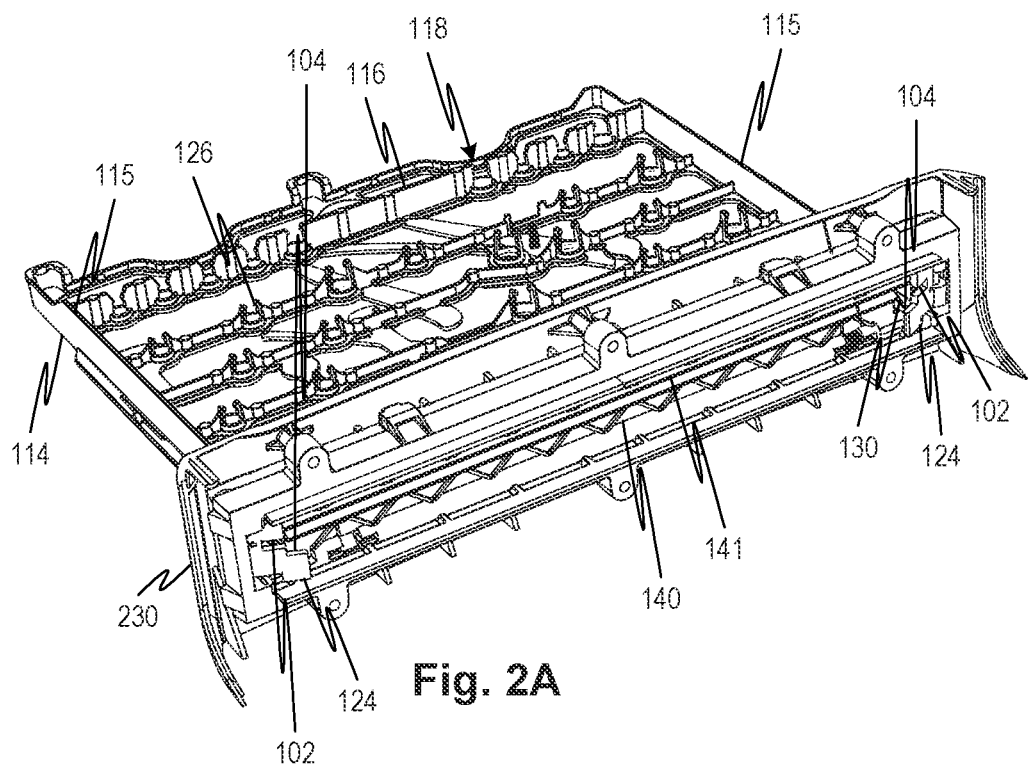
FIGS. 2A, 2B, and 2C show the cartridge chassis of FIGS. 1A, 1B, and 1C partially loaded into a slot opening of a medical treatment device with only a portion of the housing of the medical treatment device being visible in drawing according to embodiments of the disclosed subject matter.

Referring to FIGS. 1A and 1B, a cartridge chassis 114 has a frame with side walls 115 and forward and rear fences 120 and 116, respectively. The cartridge chassis 114 has a generally rectilinear shape with generally uniform depth, the depth direction being indicated at 157 in FIG. 1A. The forward fence 120 sits just behind a pair of pressure pod supports 122. The pressure pod supports 122 are located just behind the tips of a pair of key pins 130, one on either side of the cartridge chassis 114. The key pins push on latches 124 partly visible through openings 125 in doors 140 and 141 that selectively close and open a slot opening 143. FIGS. 1A and 1B show the cartridge chassis 114 immediately prior to being inserted in the slot opening 143. As the cartridge chassis 114 is moved toward the slot opening 143 in housing portion 230, the key pins 130 pass into openings 125 to push on latches 124 causing them to swing to the side on hinges whose axes are perpendicular to the longitudinal axis of the slot opening 143 in housing portion 230. The latches 124 are visible from the opposite side of the housing portion 230 as shown in FIGS. 1A and 2A. Detente pins 231 are supported resiliently on the cartridge chassis 114 so that they can engage a recess in a receiving slot (not shown).

The doors may have springs to bias them toward a closed position. The chassis keeps the doors open when the cartridge chassis 114 is fully inserted. As the cartridge chassis 114 is withdrawn the doors prevent the latches from closing by remaining in interfering engagement therewith such that the latches 124 cannot close before the doors close. Thus the latches 124 are the first to open and the last to close when the cartridge chassis 114 is pushed in and when the cartridge chassis 114 is withdrawn.

Figure 2B:
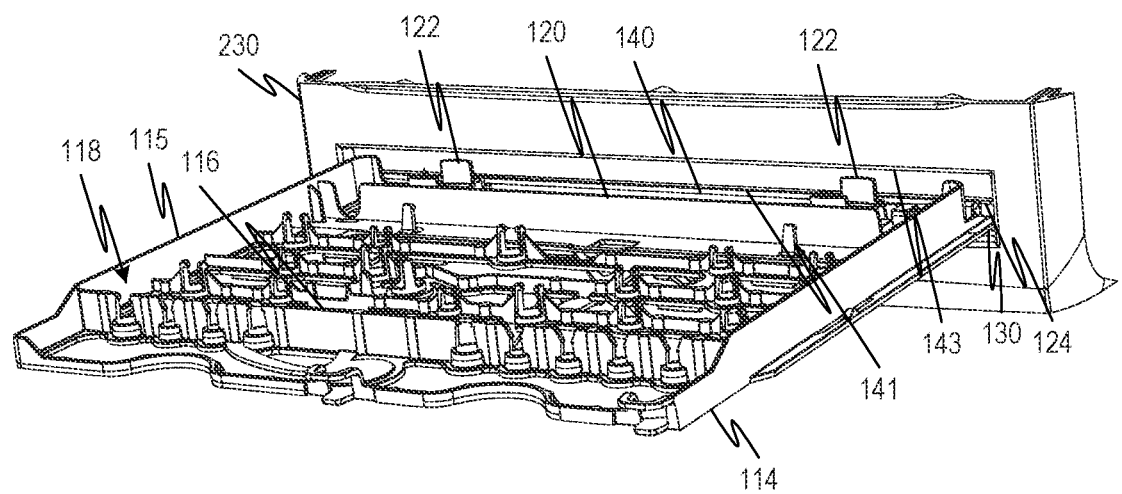
Figure 2C:
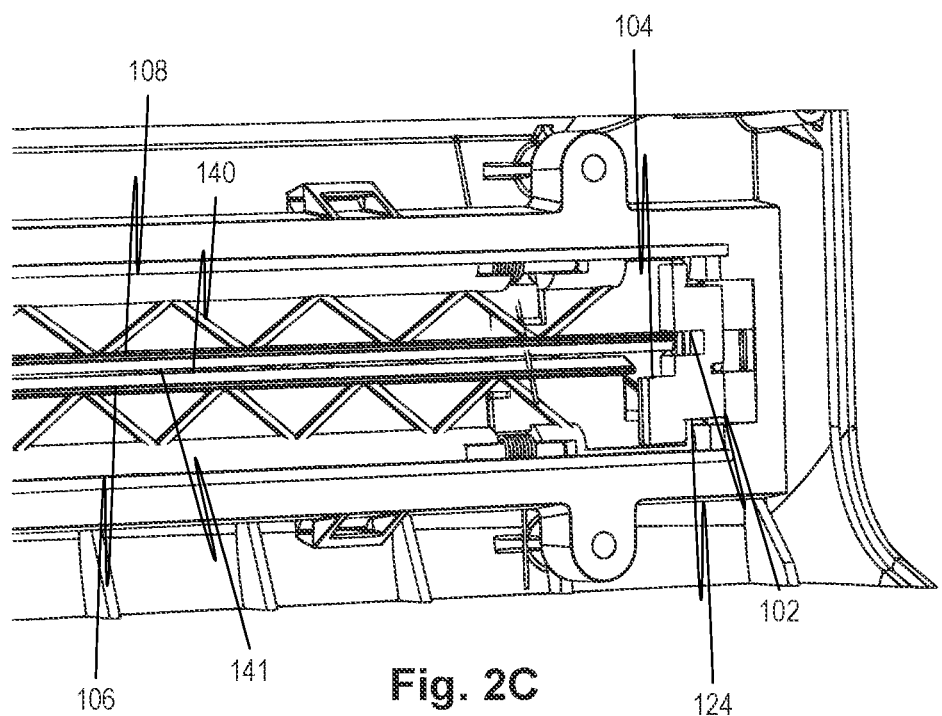

Note that FIGS. 2A, 2B, and 2C show the cartridge chassis 114 partly pushed into the slot opening 143 such that the key pins 130 have engaged the latches 124 and partially pushed them to the side thereby releasing the doors 140 and 141 such that the cartridge chassis 114 can push the doors 140 and 141 open and hold them open while inside the slot opening 143. Side walls 115 span the entire depth of the chassis such that the doors 140 and 141 are held completely open while the cartridge chassis 114 is inserted in the slot opening 143.

The latches 124 have edges 102 and 104 that interferingly engage ridges 106 and 108 to hold the doors 140 and 141 closed. When the latches 124 are pushed to the side these edges 102 and 104 are moved to the said allowing the doors 140 and 141 to open as the cartridge chassis 114 is urged into the slot opening 143 by a user.

Figure 1D:
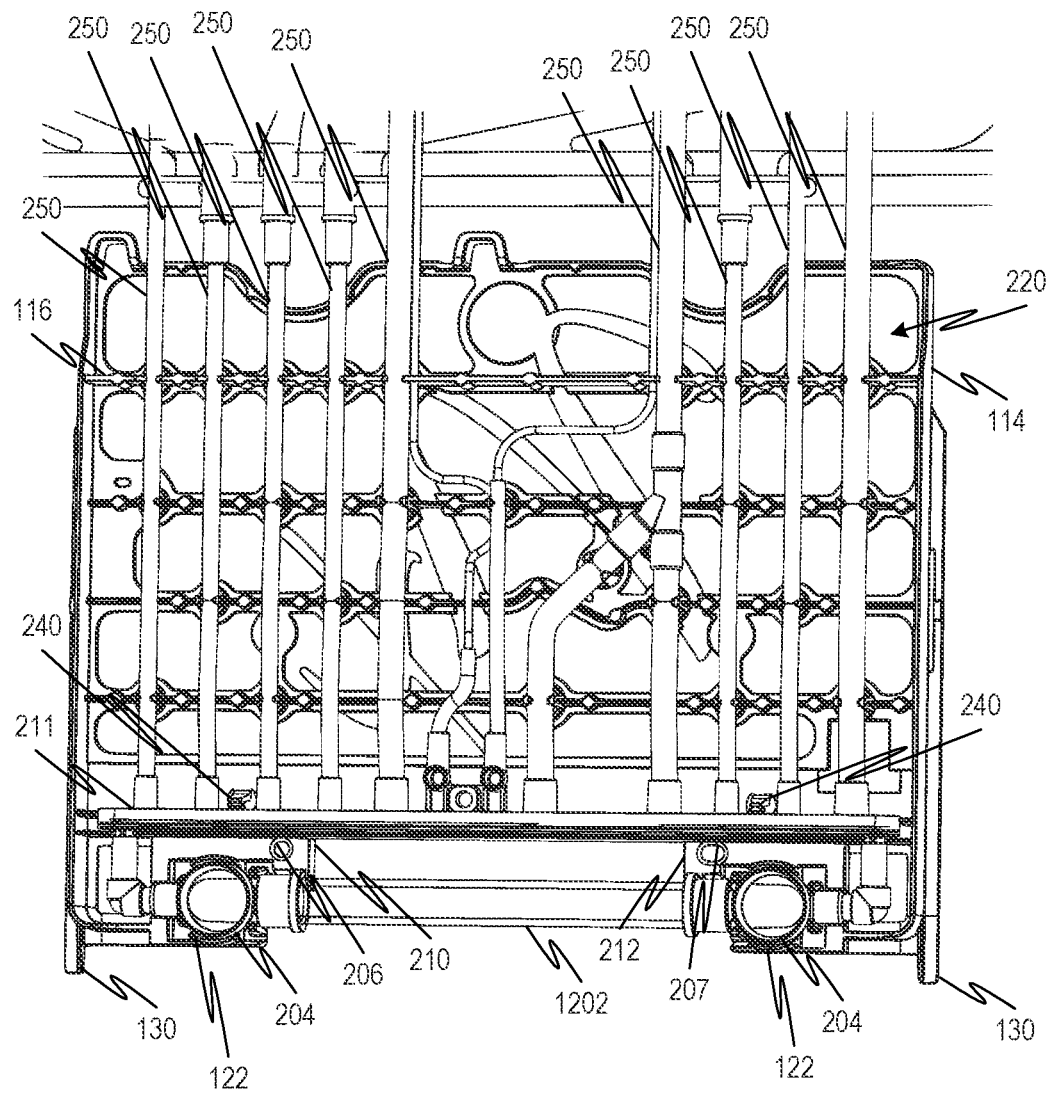
FIG. 1D shows a cartridge chassis of the embodiments of FIGS. 1A, 1B, and 1C, with fluid circuit elements attached thereto according to embodiments of the disclosed subject matter.

Note that FIGS. 1A-1C, 2A-2C and 3 show the cartridge chassis 114 with no fluid circuit 220 whilst FIG. 1D shows the cartridge chassis 114 with a fluid circuit 220. The fluid circuit 220 is attached to the cartridge chassis 114 when the device is fully manufactured as a system and while in use but in order to illustrate the function of the door latching system, the fluid circuit is omitted in FIGS. 1A through 1C. Tubes of the fluid circuit 220 are held by an array of clips 126 and slots 118 in the rear fence 116. As visible in FIG. 1D, pressure pods 204 are held by pressure pod supports 122. The pressure pod supports 122 are supported on tabs 210 and 212 that have locator holes 206 and 207, respectively. A pumping tube segment 1202 runs between the pressure pods 204 spanning a separation between the tabs 210 and 212. The pumping tube is supported by the pressure pods which are in turn supported by tabs 210 and 212. The locator hole 206 is round and the locator hole 207 is oval shaped. The oval shape provides some compliance to accommodate manufacturing variation with respect to the positions of alignment pins that are inserted in the locator holes 206 and 207 when the cartridge chassis 114 is inserted completely through the slot opening 143. The fluid circuit 220 has a manifold portion 211 that is held in the cartridge chassis 114 by clips 240.

Referring to FIG. 1D, the fluid circuit 220 has an array of tubes 250 extending from the manifold portion 211 that run to and extend beyond the rear fence 116 and extend straight rearwardly. When the cartridge chassis 114 is fully inserted, the tubes extend away from the slot opening 143. The rear fence 116 aligns with the mouth of the slot opening 143 when the cartridge chassis 114 is fully inserted such that the slot opening 143 is substantially covered by the rear fence 116. It can be seen in FIG. 1D that the key pins 130 extend beyond the pressure pod supports 122 and as such are thereby able to make contact with the latches 124 before the cartridge chassis 114 makes contact with the doors 140 and 141 as the cartridge chassis 114 is progressively pushed into the slot opening 143. The length of the key pins 130 is such that the latches 124 are swung far enough aside that the doors 140 and 141 are released to open before the cartridge chassis 114 makes contact with the doors. Thereafter, the doors are held open by the side walls 115 and the bottom of the cartridge chassis 114.

Figure 3:
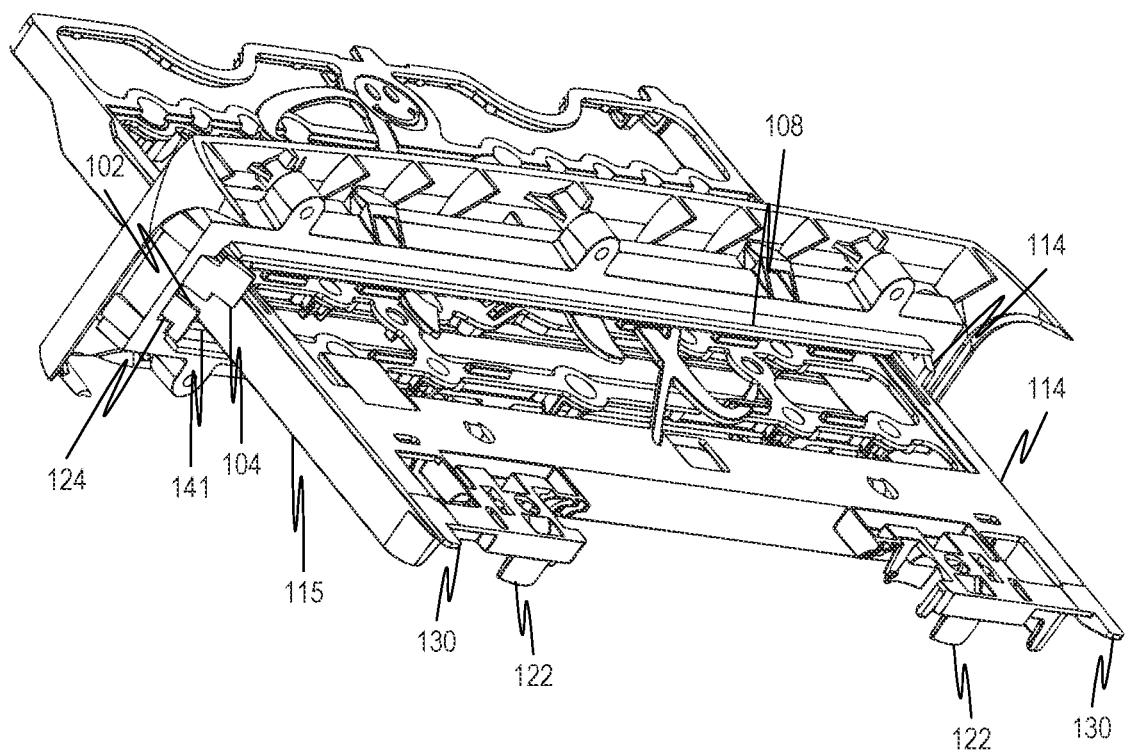
FIG. 3 shows the cartridge chassis of FIGS. 1A, 1B, and 1C substantially loaded into the medical treatment device according to embodiments of the disclosed subject matter.

In FIG. 3, the cartridge chassis 114 has been inserted substantially, but not fully, through the slot opening 143 so that the latches 124 are pivoted to the side. The doors 140 and 141 are fully held apart by the side walls 115 and the cartridge chassis 114 bottom (the cartridge chassis 114 bottom facing upward from the viewpoint of FIG. 3).

Figure 4A:
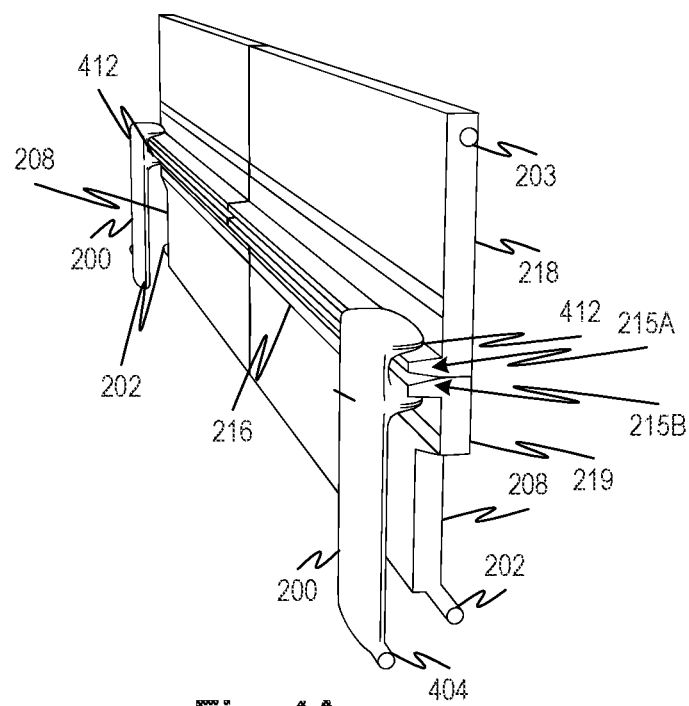
FIGS. 4A, 4B, 4C and 4D show a latch and door mechanism in various configurations before and after insertion of a chassis with respective keys according to embodiments of the disclosed subject matter.
Figure 4B:
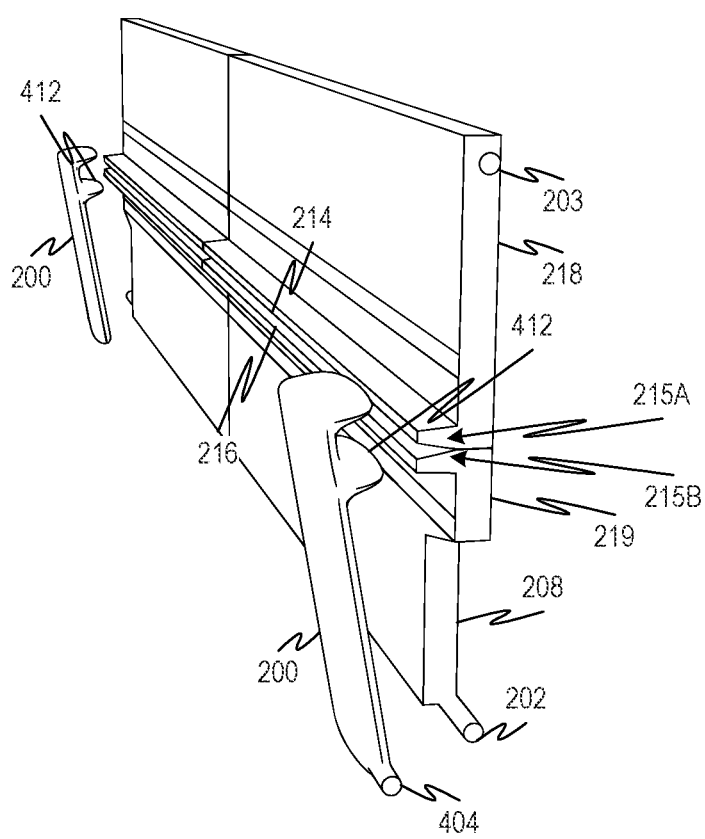
Figure 4C:
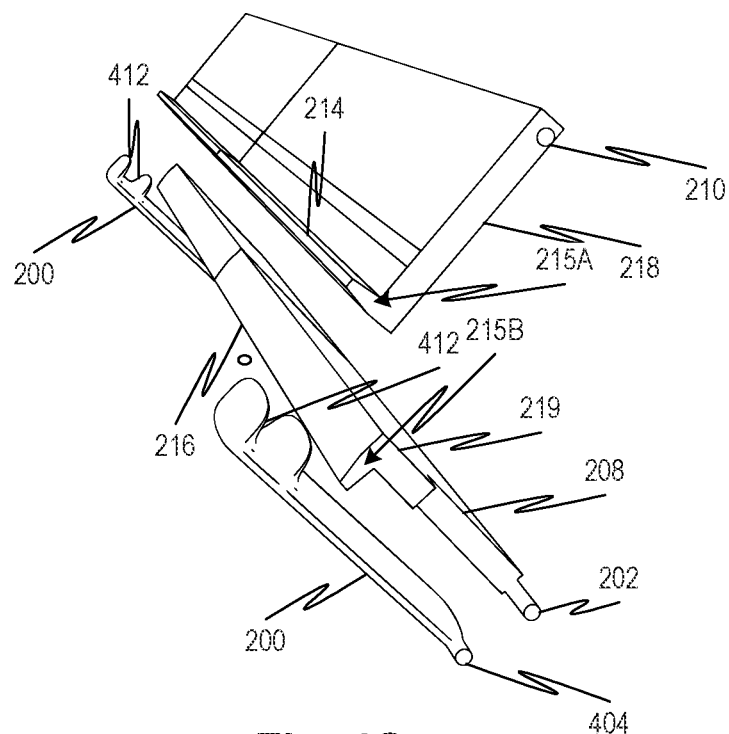
Figure 4D:
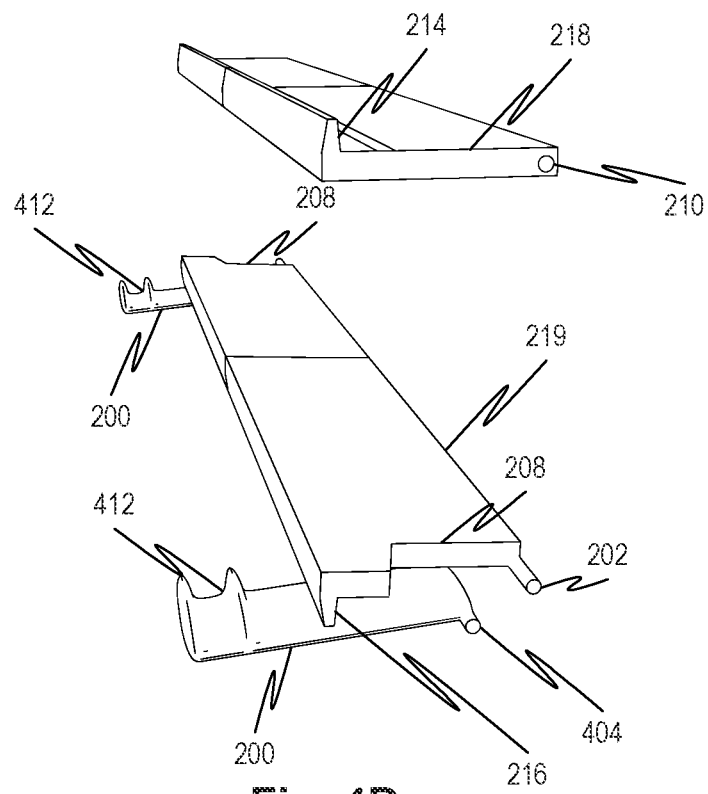

Referring now to FIG. 4A, a door 218 is held closed with a door 219 by jaws 412 of two latches 200, one at either end of the doors 218 and 219. The doors 218 and 219 are held closed because edges 214 and 216 on ridges 215A and 215B on the doors 218 and 219 remain in interfering engagement with the jaws 412. The door 219 has a cutout 208 near a hinge 202 (shown as a pivot pin) of the door 219 at each end thereof. Door 218, on the other hand, does not need a cutout near its hinge 203, in this embodiment. The latches 200 pivot on respective pins 404. When keys of a chassis (not shown in the present drawing but similar to those shown in the previous embodiments) are inserted through the cutouts 208, the latches 200 are forced away from the ridges 215A and 215B releasing the doors 218 and 219 as shown in FIG. 4B. As shown in FIG. 4C, as the chassis (not shown) is pushed further, the door 219 pushes the latches 200 out of the way as the chassis is forced against the door 219. The door 218 is similarly to the side. FIG. 4D shows the positions of the doors 218 and 219 after being forced open by the chassis. The removal of the chassis results in the reverse sequence. It will be observed that the latches 200 are the first to open and the last to close as in the embodiments described above.

It will be appreciated that the embodiment in FIGS. 4A and 4B can be modified to omit one of the latches 200, while retaining its functionality. Furthermore, a third latch 200 could be added, for example near the middle of the doors, with a corresponding cutout in the appropriate door, to create a more unique key pattern that needs to be matched before the doors open and permit a cartridge to be inserted. This is particularly advantageous to prevent the insertion of incorrect cartridges into the system.

According to first embodiments, the disclosed subject matter includes a cartridge insertion system. In the system, a chassis supports a fluid circuit. The chassis has a forward end with key pins projecting from the forward edge and a rear end. A medical treatment device has a slot opening closed by doors, the doors having key openings spaced apart a same distance as the key pins such that when the chassis is pushed toward the slot opening, the key pins enter the key openings before the forward end meets the doors. Latches on the medical treatment device immediately behind the key openings each configured to pivot on a latch axis. The doors pivoting on door axes parallel to the major dimension. The latches and doors are configured to interfere such that when the latches are closed, prior to contact with the key pins, the doors are prevented from opening and such that when the key pins push against the latches, the latches swing to one side, releasing the doors.

The first embodiments can be modified to form additional first embodiment in which the key openings are located to one side of a major dimension of the slot opening. The first embodiments can be modified to form additional first embodiment in which the latch axis is perpendicular to the major dimension. The first embodiments can be modified to form additional first embodiment in which the latches have opposing facing edges that engage with ridges on the doors when the doors are closed and the latches are in a home position prior to being pushed by the key pins. The first embodiments can be modified to form additional first embodiment in which the cartridge holds the doors open and the doors are spring loaded to close such that when the latches return to a home position the doors are locked and prevent objects from being inserted. The first embodiments can be modified to form additional first embodiment in which the cartridge holds the doors open and the doors are spring loaded to close such that when the latches return to a home position the doors are locked and prevent objects from being inserted. The first embodiments can be modified to form additional first embodiment in which the objects are fingers thereby preventing a hazard. The first embodiments can be modified to form additional first embodiment in which the fluid circuit has tubes that project away from the rear end extending beyond the rear end to connect to connectors remote from the chassis. The first embodiments can be modified to form additional first embodiment in which the tubes are generally parallel.

The first embodiments can be modified to form additional first embodiment in which the chassis projects partly from the slot, opening when fully inserted in the medical treatment device. The first embodiments can be modified to form additional first embodiment in which the fluid circuit includes a pumping tube segment connected to the chassis. The first embodiments can be modified to form additional first embodiment in which the pumping tube segment is positioned parallel to the major dimension when the chassis is oriented for insertion in the slot opening. The first embodiments can be modified to form additional first embodiment in which the pumping tube segment lies between a major portion of the chassis and a line connecting tips of the key pins. The first embodiments can be modified to form additional first embodiment in which the pumping tube segment is attached to pressure pods at either end of the pumping tube segment. The first embodiments can be modified to form additional first embodiment in which the pumping tube segment is supported by the pressure pods.

The first embodiments can be modified to form additional first embodiment in which the pressure pods are supported by tabs extending from the chassis, the tabs having locator holes. The first embodiments can be modified to form additional first embodiment in which the chassis has a rear fence with slots for the tubes. The first embodiments can be modified to form additional first embodiment in which the rear fence is aligned with the slot opening when the chassis is fully inserted in the medical treatment device. The first embodiments can be modified to form additional first embodiment in which the chassis has detente pins along opposite sides thereof between the forward end and the back end, the detente pins being supported resiliently so as to flex when pushed. The first embodiments can be modified to form additional first embodiment in which the chassis has a generally uniform depth, the depth being perpendicular to two major dimensions thereof. The first embodiments can be modified to form additional first embodiment in which the doors prevent the latches from closing by remaining in interfering engagement therewith such that the latches cannot close before the doors close. The first embodiments can be modified to form additional first embodiment in which, when the chassis is inserted in the slot opening, the latches are the first to open and when the chassis withdrawn from the slot opening, latches are the last to close.

According to second embodiments, the disclosed subject matter includes a cartridge in which a chassis supports a fluid circuit, the chassis having a forward end with key pins projecting from the forward edge and a rear end. The fluid circuit has tubes that project away from the rear end extending beyond the rear end to connect to fluid circuit portions remote from the chassis. The chassis has a rear fence inboard of a the rear end. The fluid circuit includes a pumping tube segment connected to the chassis. The pumping tube segment lies between a major portion of the chassis and a line connecting tips of the key pins.

The second embodiments can be modified to form additional second embodiments including the cartridge described above, wherein the pumping tube segment is attached to pressure pods at either end of the pumping tube segment. The second embodiments can be modified to form additional second embodiment in which the pressure pods are supported by tabs extending from the chassis, the tabs having locator holes. The second embodiments can be modified to form additional second embodiment in which the tubes are generally parallel.

The second embodiments can be modified to form additional second embodiment in which the pumping tube segment is attached to pressure pods at either end of the pumping tube segment. The second embodiments can be modified to form additional second embodiment in which the pumping tube segment is supported by the pressure pods.

The second embodiments can be modified to form additional second embodiment in which the chassis has a rear fence with slots for the tubes. The second embodiments can be modified to form additional second embodiment in which the rear fence is aligned with the slot opening when the chassis is fully inserted in the medical treatment device. The second embodiments can be modified to form additional second embodiment in which the chassis has detente pins along opposite sides thereof between the forward end and the back end, the detente pins being supported resiliently so as to flex when pushed.

It is, thus, apparent that there is provided, in accordance with the present disclosure, medical device loading systems, devices, and methods. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A cartridge insertion system, comprising:
    a chassis supporting a fluid circuit, the chassis having a forward end with key pins projecting from said forward end and a rear end;
    a medical treatment device having a slot opening closed by doors having a major dimension, the doors having key openings spaced apart a same distance as said key pins such that when said chassis is pushed toward said slot opening, said key pins enter said key openings before said forward end meets said doors;
    latches on said medical treatment device immediately behind said key openings, each of the latches configured to pivot on a latch axis;
    the doors pivoting on door axes parallel to the major dimension; and
    the latches and the doors being configured to interfere such that when the latches are closed in a home position, prior to contact with said key pins, the doors are prevented from opening and such that when said key pins push against said latches, the latches move to one side, releasing the doors.

2. The system of claim 1, wherein said key openings are located to one side of the major dimension of said slot opening.

3. The system of claim 1, wherein said latch axis is perpendicular to said major dimension.

4. The system of claim 1, wherein said latch axis is parallel to said major dimension.

5. The system of claim 1, wherein said latches have opposing facing edges that engage with ridges on said doors when the doors are closed and the latches are in the home position prior to being pushed by the key pins.

6. The system of claim 5, wherein the cartridge holds the doors open and the doors are spring loaded to close such that when the latches return to the home position the doors are locked and prevent objects from being inserted.

7. The system of claim 1, wherein the cartridge holds the doors open and the doors are spring loaded to close such that when the latches return to the home position the doors are locked and prevent objects from being inserted.

8. The system of claim 1, wherein the fluid circuit has tubes that project away from said rear end extending beyond said rear end to connect to connectors remote from said chassis, and
    said tubes are generally parallel.

9. The system of claim 1, wherein said fluid circuit includes a pumping tube segment connected to the chassis.

10. The system of claim 9, wherein the pumping tube segment is positioned parallel to said major dimension when the chassis is oriented for insertion in said slot opening.

11. The system of claim 9, wherein said pumping tube segment lies between a major portion of the chassis and a line connecting tips of said key pins.

12. The system of claim 9, wherein said pumping tube segment is attached to pressure pods at either end of the pumping tube segment.

13. The system of claim 1, wherein said chassis has a rear fence with slots for tubes, and
    said rear fence is aligned with the slot opening when said chassis is fully inserted in said medical treatment device.

14. The system of claim 1, wherein the chassis has a generally uniform depth, the depth being perpendicular to two major dimensions thereof.

15. The system of claim 1, wherein the doors prevent the latches from closing by remaining in interfering engagement therewith such that the latches cannot close before the doors close.

16. The system of claim 1, wherein, when the chassis is inserted in the slot opening, the latches are first to open and when the chassis withdrawn from the slot opening, the latches are last to close.

* * * * *